United States Patent [19]

Donadello

[11] Patent Number: 5,041,628

[45] Date of Patent: Aug. 20, 1991

[54] METHOD FOR THE PREPARATION OF N-PHOSPHONOMETHYL GLYCINE

[75] Inventor: Graziello Donadello, Vicenza, Italy

[73] Assignee: Finchimica S.p.A., Manerbio, Italy

[21] Appl. No.: 537,652

[22] Filed: Jun. 14, 1990

[30] Foreign Application Priority Data

Jun. 15, 1989 [IT] Italy ................... 67489 A/89

[51] Int. Cl.$^5$ ............................................. C07F 9/38
[52] U.S. Cl. ................................................. 562/17
[58] Field of Search .......................................... 562/17

[56] References Cited

U.S. PATENT DOCUMENTS

| | | | |
|---|---|---|---|
| 2,796,443 | 6/1957 | Meyer et al. | 568/851 |
| 4,065,491 | 12/1977 | Pfliegel et al. | 260/502.5 F |
| 4,237,065 | 12/1980 | Ehrat | 260/502.5 F |
| 4,439,373 | 3/1984 | Nagubandi | 260/502.5 F |
| 4,486,359 | 12/1984 | Hajnoczki et al. | 260/502.5 F |

FOREIGN PATENT DOCUMENTS

| | | | |
|---|---|---|---|
| 97522 | 1/1984 | European Pat. Off. | 260/17 |
| 1062210 | 12/1983 | U.S.S.R. | 562/17 |

OTHER PUBLICATIONS

The Merck Index, 8th ed. (1968) pp. 4–69.

*Primary Examiner*—J. E. Evans
*Attorney, Agent, or Firm*—Rothwell, Figg, Ernst & Kurz

[57] ABSTRACT

N-phosphonomethyl glycine is prepared by the reaction of glycine with an aqueous-alcoholic solution of formaldehyde in the presence of a base selected from the group consisting of alkali and alkaline-earth metal hydroxides, the reaction of the solution thus obtained with a trialkylphosphite and hydrolysis in an aqueous medium, with recovery of the N-phosphonomethyl glycine by crystallization.

7 Claims, No Drawings

METHOD FOR THE PREPARATION OF N-PHOSPHONOMETHYL GLYCINE

The present invention relates to a method for the preparation of N-phosphonomethyl glycine by the phosphonomethylation of glycine.

N-phosphonomethyl glycine (Merck Index X edition, N. 4376), otherwise known as glyphosate, and its derivatives are wide-spectrum herbicides which are particularly effective in controlling and modifying the growth of a wide variety of plant species.

Numerous routes have been proposed for the synthesis of N-phosphonomethyl glycine, such as:
- methods which use iminodiacetic acid as the starting material,
- methods which use N-trisubstituted triazine, and
- methods for the phosphonomethylation of glycine.

With reference to this latter route, to which the present invention relates in particular, U.S. Pat. No. 4,065,491 describes a method which comprises the condensation of glycine, formaldehyde and a dialkyl phosphite in an aqueous alkaline solution to form a dialkyl ester of N-phosphonomethyl glycine which is then hydrolised with a strong mineral acid.

As already recognised in U.S. Pat. No. 4,486,359, because dialkyl phosphites decompose easily in water, this method has serious operational difficulties and produces low yields when carried out on a commercial scale.

The reaction between glycine, formaldehyde and a phosphite carried out in an acid environment leads mainly to the formation of glyphosine.

In order to avoid these problems, U.S. Pat. No. 4,237,065 operates in an essentially anhydrous environment with methanol as the solvent and a tertiary amine (triethylamine) to keep it at a basic pH and makes use of paraformaldehyde which is depolymerised "in situ" by the alkalinity the triethylamine itself. Subsequent alkaline hydrolysis, carried out in excess caustic soda, is then necessary to recover the methanol and triethylamine which are re-used.

U.S. Pat. No. 4,486,359 describes and claims a method including the formation of a dimethylol derivative of glycine by the reaction of glycine and formaldehyde in a basic and, at least initially, anhydrous environment, the reaction of this derivative with dialkylphosphite to form a new alkylphosphite, N-methylene, N-hydroxymethylene glycine, the subjection of this intermediate to acid "transposition-hydrolysis" at low temperature and finally its hydrolisation to glyphosate.

In this case, in order to maintain the essential, initial anhydrous condition, the source of formaldehyde is again paraformaldehyde which is depolymerised in situ.

This method requires an additional operation—the "transposition-hydrolysis"—which has to be carried out with a strong acid. Like the method of U.S. Pat. No. 4,237,065, it does not allow acid or basic hydrolysis to be selected according to the circumstances. In order to achieve good results, it is thus necessary to use triethylamine and the method is therefore particularly onerous both in terms of energy and of the plant needed for the recovery of the triethylamine and methanol in the absolutely anhydrous condition required for the process itself.

The efforts made to introduce methods which use less dangerous starting materials and which are thus themselves safer are also known.

The U.S. National Toxicology Program has recently published a toxicological study which shows from experiments in rats that dimethylphosphite has a significant carcinogenic effect.

Formaldehyde is also thought to be "a suspect carcinogen in man" and is thus strictly controlled, and exposure to formaldehyde must be avoided and reduced to the lowest values technologically possible; and, as is well known to experts, since it is much more difficult technically to exclude or minimise contamination with a solid than with a liquid in plant operation and maintenance and in storage and handling, it is preferable to use formaldehyde in solution instead of obtaining it from the depolymerisation of paraformaldehyde.

U.S. Pat. No. 4,439,373, which relates to the preparation of phosphonomethylated aminoacids proposes the use of phosphites, di- and tri-substituted with alkyl, phenyl and substituted phenyl groups, as the source of phosphorus but with the reaction of the primary amino acid after the primary amino group has been protected by a carboxylic protector group which is subsequently removed.

The trialkylphosphite is used, however, in a rigorously anhydrous environment.

It has now been discovered that it is possible to carry out the condensation of formaldehyde with glycine in an aqueous-alcoholic medium, in the presence of a base constituted by an alkali or an alkaline earth metal hydroxide, with the use of a trialkylphosphite, which is a particularly advantageous source of phosphorus, as the phosphorus source.

The use of a trialkylphosphite has various advantages:

1—it is cheaper than dialkylphosphites
2—it does not have the toxicity risks of dialkylphosphites
3—it is quite stable under hydrolysis both in neutral and in alkaline media.

As a result of the stability of trialkylphosphites to hydrolysis, the commercial solution of 55% formaldehyde in methanol (35%) and water (10%), which is very easy to measure and presents less risk in movement, handling and in use, can be used as the formaldehyde source.

98% commercial caustic soda or, even better, 85% commercial caustic potash can be used to control the pH of the reaction and to dissolve the glycine.

The use of caustic potash in particular drastically reduces the salinity of the waste liquids and enables KCl, of a quality used universally as a fertiliser, to be obtained as a by-product.

Methanol is used as the solvent because of its cheapness but its recovery is less expensive in that anhydrous conditions are not necessary.

The "dimethylol derivative" of glycine does not form in the reaction conditions and hydrolysis can therefore be carried out either with acids or with bases.

The subject of the invention is therefore a method for the preparation of N-phosphonomethyl glycine by the phosphonomethylation of glycine in an aqueous-alcoholic solution, characterised in that it comprises the steps of:

reacting glycine with an aqueous-alcoholic solution of formaldehyde in the presence of a base selected from the group consisting of alkali and alkaline-earth metal hydroxides, reacting the solution thus obtained with trialkylphosphite, and effecting hydrolysis in an aqueous environment and recovering the N-phosphonomethyl glycine by crystallisation.

The formaldehyde source used is a commercial 55% solution in aqueous methanol.

The glycine-formaldehyde molar ratio may be varied between 1:1 and 1:2 according to whether it is more convenient to increase the yield with respect to the glycine or to the trialkylphosphite.

With a molar ratio of 1:1, glycine can be recovered from the reaction mixture for re-use in subsequent operations.

Sodium hydroxide, potassium hydroxide or possibly calcium hydroxide are preferably used as the hydroxide in quantities such as to produce a pH of between 6.5 and 8.5.

The trialkylphosphite is preferably added to the solution under hot conditions in order to avoid secondary reactions.

When the reaction of the trialkylphosphite has finished, the subsequent hydrolysis can be carried by alkaline hydrolysis, acid hydrolysis or in an aqueous environment under pressure. Acid hydrolysis is carried out by the addition of a strong mineral acid, preferably hydrochloric acid, in moderate concentrations, but not less than 20%, which causes the precipitation of the chloride of the alkali metal constituent of the hydroxide used. The mineral acid is then removed by distillation and N-phosphonomethyl glycine is obtained by crystallisation from water.

The hydrolysis can also be carried out with water, possibly with the addition of a small quantity of acid, preferably a non-volatile acid such as sulphuric acid; in this case, however, a temperature considerably higher than 100° C., for example 110°-120° C., is desirable and it is therefore necessary to operate under pressure. With the use of hydrochloric acid, however, it is convenient to operate at the boiling point of the azeotropic water-/acid mixture (about 115° C.).

Alkaline hydrolysis requires the addition of an alkaline hydroxide, followed by acidification with strong mineral acid to crystallise the N-phosphonomethyl glycine.

The basic hydrolysis is preferably carried out at a temperature of between 70° and 80° C., at a pH of between 11 and 11.5, after which the alcoholic solvent is removed by distillation at a temperature below 80° C.

The acidification with strong mineral acid is then carried out at ambient temperature to a pH of between 1.5 and 1.7.

EXAMPLE 1

1000 ml of methanol and 40 g (1 mole) of sodium hydroxide were added dropwise to a 2-liter, multi-necked flask provided with a stirrer, a thermometer, a separating funnel and a reflux condenser, the whole protected from humidity. The mixture was stirred until the hydroxide had dissolved completely; as a result of its dissolving, the temperature rose to 40° C. At this temperature, 110 g (2 moles) of 55% formaldehyde were added. 75 g (1 mole) of glycine were added and the mixture was heated to 60° C. for 15 minutes. When the glycine had dissolved, 124 g (1 mole) of trimethylphosphite were added dropwise over about 60 minutes, the reflux temperature being maintained and, at the end of the addition, the mixture was refluxed under agitation for 2.5 hours. The mixture was cooled to ambient temperature and 350 ml of 36% hydrochloric acid were poured in. The mixture was kept at 10°-15° C. for 30 minutes, the sodium chloride which precipitated was filtered off, the cake was washed with a little methanol and 43 g of sodium chloride were recovered.

The filtrate was decanted quantitatively into the flask, the condenser was arranged in the distillation position, the filtrate was stirred and the solvent was distilled off until the internal temperature reached 110°-113° C. These conditions were maintained for 2.5 hours.

The mixture was distilled under vacuum until a viscous residue was obtained. This was taken up with 100 ml of water and distilled again under vacuum almost to dryness. This operation was repeated once more to enable almost all the hydrochloric acid to be removed. The mass was taken up with 200 ml of water and left to crystallise for 18 hours at 8°-10° C. The crystals were filtered off and washed with water. The cake of dried glyphosate weighed 83 g and had a melting point of 238° C.

EXAMPLE 2

The method of Example 1 was used and, after the trimethylphosphite had been added and the solution had been refluxed with stirring for 2.5 hours, the condenser was arranged in the distillation position and 260 g of a 30% solution of sodium hydroxide were introduced through the separating funnel over 45 minutes. The methanol was distilled simultaneously until the internal temperature reached 90°-95° C.

The mixture was cooled to 30°-40° C. and this temperature was maintained whilst the mixture was acidified with 350 ml of 36% hydrochloric acid until the pH of the mixture was 1.5.

20 ml of 36% $H_2O_2$ were added and the mixture was boiled for 30 minutes. The mixture was left to crystallise for 18 hours at 8°-10° C. The crystals were filtered off and the panel of glyphosate washed with water. The dried glyphosate cake weighed 75 g and had a melting point of 226°-228° C.

Although only trimethyl phosphite was used in the examples described, alkyl phosphites in which the alkyl group has from 1 to 4 carbon atoms may be used.

EXAMPLE 3

1350 ml of methanol and 76.5 g of 88% KOH (1.2 moles) were introduced into a 3-liter, multi-necked flask provided with a stirrer, a thermometer, a separating funnel and a reflux condenser, the whole protected from humidity.

The mixture was stirred until the solids had dissolved completely and then 109 g of a 55% aqueous methanolic solution of formaldehyde (2.0 moles) and 150 g of glycine (2.0 moles) were added.

The mixture was stirred until a solution was obtained, brought to reflux temperature and 165 g of trimethylphosphite were added over about 60 minutes and refluxing was continued for a further 3 hours.

The mixture was cooled to ambient temperature and 120 g of 36% HCl were added and after 30 minutes the mixture was filtered.

The precipitate was washed with methanol and dried. It contained 59 g of glycine as well as the KCl.

25 g of 98% $H_2SO_4$ was added to the filtrate and the methanol was distilled off until the temperature reached 90°-95°.

The residue was placed in an autoclave and heated under pressure to 110°-115° C. for 4 hours.

HPLC analysis showed that the hydrolysis was complete and the solution contained 128 g of glyphosate.

What is claimed is:

1. A method for the preparation of N-phosphonomethyl glycine by the phosphonomethylation of glycine in an aqueous-alcoholic solution, wherein said method comprises the steps of:

reacting glycine with an aqueous-alcoholic solution of formaldehyde in the presence of a base selected from the group consisting of alkali and alkaline-earth metal hydroxides, reacting the solution thus obtained with a trialkylphosphite, and effecting hydrolysis in an aqueous medium and the recovering said N-phosphonomethyl glycine by crystallisation.

2. A method according to claim 1, wherein said hydrolysis is carried out by the addition of an alkaline hydroxide followed by acidification with a strong mineral acid.

3. A method according to claim 1, wherein said hydrolysis is carried out by the addition of a strong mineral acid in an aqueous medium followed by removal of the mineral acid by distillation and crystallisation of said N-phosphonomethyl glycine from water.

4. A method according to claim 1, wherein said hydrolysis is carried out in a medium selected from an aqueous medium and an acidified aqueous medium, at a temperature above 110° C. and under pressure.

5. A method according to claim 1, wherein the alkyl group in the trialkylphosphite has from 1 to 4 carbon atoms.

6. A method according to claim 1, wherein said base is selected from the group consisting of sodium hydroxide and potassium hydroxide.

7. A method according to claim 1, wherein the alcoholic solvent in said aqueous-alcoholic solution is methanol.

* * * * *